(12) United States Patent
Mahashabde et al.

(10) Patent No.: US 7,005,138 B2
(45) Date of Patent: Feb. 28, 2006

(54) METHOD OF SYSTEMATICALLY DELIVERING SSRIS

(75) Inventors: Anu Mahashabde, Kendall Park Township, Middlesex County, NJ (US); Martha Francine Kay, Lawrenceville Township, Mercer County, NJ (US); Brian Glazer, Franklin Township, Somerset County, NJ (US); Junxiong Zhang, Montgomery Township, Somerset County, NJ (US)

(73) Assignee: Duramed Pharmaceuticals, Inc., Cincinnati, OH (US)

( * ) Notice: Subject to any disclaimer, the term of this patent is extended or adjusted under 35 U.S.C. 154(b) by 316 days.

(21) Appl. No.: 10/095,558

(22) Filed: Mar. 12, 2002

(65) Prior Publication Data

US 2003/0133977 A1   Jul. 17, 2003

Related U.S. Application Data

(60) Provisional application No. 60/343,254, filed on Dec. 21, 2001.

(51) Int. Cl.
A61F 13/00 (2006.01)
A61F 6/06 (2006.01)
A61F 6/14 (2006.01)

(52) U.S. Cl. ............. 424/434; 424/422; 424/430; 424/432

(58) Field of Classification Search ........... 424/422, 424/430, 432, 434
See application file for complete search history.

(56) References Cited

U.S. PATENT DOCUMENTS

| 4,012,496 | A * | 3/1977 | Schopflin et al. | |
| 6,228,875 | B1 * | 5/2001 | Tsai et al. | |
| 6,239,162 | B1 | 5/2001 | Oxenkrug | |
| 6,264,973 | B1 * | 7/2001 | Mahashabde et al. | |
| 6,331,571 | B1 * | 12/2001 | Jerussi et al. | |
| 2002/0192302 | A1 * | 12/2002 | Hsu et al. | 424/719 |
| 2003/0139381 | A1 * | 7/2003 | Bell et al. | 514/170 |

* cited by examiner

Primary Examiner—Thurman K. Page
Assistant Examiner—Humera N. Sheikh
(74) Attorney, Agent, or Firm—Gibbons, Del Deo, Dolan, Griffinger and Vecchione

(57) ABSTRACT

Methods and compositions are disclosed for the intravaginal or rectal delivery of selected serotonin reuptake inhibitors (SSRIs) to the systemic circulation. Such methods and compositions are useful in the treatment of depression, migraine headaches, chronic pain, psychoactive substance abuse disorders, pre-menstrual dysphoric disorder (PMDD) and obsessive compulsive disorders. The compositions may be formulated for the immediate release or controlled release of SSRIs over an extended period of time. A preferred SSRI is fluoxetine.

12 Claims, 9 Drawing Sheets

VARIABLE LENGTH SLOT DEPENDING ON THE DESIRED DOSE

METHOD OF SYSTEMATICALLY DELIVERING SSRIS

RELATED APPLICATIONS

This application is a continuation of Provisional Patent Application No. 60/343,254 filed Dec. 21, 2001.

FIELD OF THE INVENTION

This invention provides methods for the systemic administration, via intravaginal or rectal modes, of selective serotonin reuptake inhibitors (SSRIs).

BACKGROUND OF THE INVENTION

Selective serotonin reuptake inhibitors (SSRIs) are a class of medication used primarily to treat psychiatric disorders, including depression, obsessive-compulsive syndromes, and others. These agents are believed to exert their therapeutic action by blocking neuronal uptake of serotonin, thereby resulting in increased levels of serotonin. Because of this mechanism of action, SSRIs often regarded as treating the symptoms of depression more effectively than other commonly prescribed antidepressant agents such as tricyclic antidepressant agents. In addition, some metabolic disorders that are affected by serotonin levels have benefited from the use of SSRIs. The most common SSRIs include fluoxetine (Prozac®), sertraline (Zoloft®), paroxetine (Paxil®), fluvoxamine (Luvox®), and citalopram (Celexa®).

A preferred SSRI is fluoxetine, which chemically is dl-N-methyl-γ-[4-(trifluoromethyl)phenoxy]benzenepropanamine. Fluoxetine is chemically unrelated to the tricyclic, tetracyclic, or other available antidepressant agents. It has an empirical formula of $C_{17}H_{18}F_3NO.HCl$, a molecular weight of 345.79 and is commonly utilized as the hydrochloride salt. Fluoxetine is a selective serotonin uptake inhibitor useful in the treatment of depression, anxiety, bulimia, obesity, obsessive compulsive syndrome and other disorders including migraine and pre-menstrual dysphoric disorder (PMDD).The antidepressant, anti-obsessive-compulsive, and anti-bulemic actions of fluoxetine are presumed to be linked to its inhibition of CNS neuronal uptake of serotonin. The most commonly observed adverse events associated with the use of fluoxetine are nausea, headache, insomnia, anxiety, nervousness, somnolence, and sexual dysfunction.

Traditionally, fluoxetine and other SSRIs have been administered orally in the form of tablets, capsules, granules, and pills. Fluoxetine oral dosages range from about 20 mg to 80 mg daily depending on the individual patient and the disorder being treated. Such oral administration inherently subjects the active agent to a first pass metabolism in the liver before permitting the SSRIs to circulate throughout the body. The half life of fluoxetine (2–3 days) and its active metabolite norfluoxetine (7–9 days) is relatively long. The primary route of elimination appears to be hepatic metabolism to inactive metabolites excreted by the kidney. The complexity of the metabolism of fluoxetine combined with the variability in metabolism of the drug among individuals has several clinical consequences. Accordingly, there is a need for a delivery method that is less dependent on metabolic variability from patient to patient, and allows for greater control over circulating levels of active agents and metabolites.

Vaginal dosage forms are known for the local administration of medicaments for the treatment of gynecological and obstetric conditions. The principal advantage of such dosage forms is that small doses of medicament can be administered locally, which is preferable to systemic treatment of the same conditions which typically requires larger doses to affect the same results. However, it is neither taught nor suggested in the literature that medicaments, such as SSRIs, could be administered via the intravaginal or rectal routes for delivery into the systemic circulation. It has been unexpectedly discovered, and thus forms the basis of the present invention, that the problems of metabolic variability with selected serotonin reuptake inhibitors alluded to above can be substantially resolved by administration via the intravaginal or rectal routes.

SUMMARY OF THE INVENTION

The invention discloses a method of systemically delivering an SSRI to a mammal which comprises administering a therapeutically effective amount of the SSRI intravaginally or rectally. Preferred SSRIs include fluoxetine, sertraline, paroxetine, fluvoxamine, citalopram and pharmaceutically acceptable salts thereof. Particularly preferred is fluoxetine and pharmaceutically acceptable salts thereof.

The present invention further includes compositions and devices for the intravaginal or rectal administration of an SSRI, for immediate or controlled release as well as the therapeutic treatment of conditions such as depression by the intravaginal or rectal administration of a composition comprising a SSRI and a pharmaceutically acceptable carrier suitable for such administration.

DETAILED DESCRIPTION OF THE INVENTION

Figure 1A:
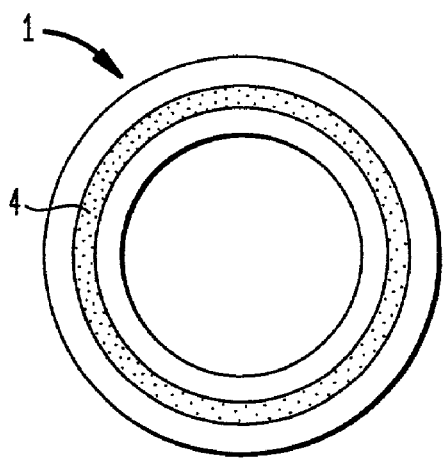
FIG. 1A is a schematic top view of a vaginal ring device.

This invention provides novel methods of systemically delivering a selective serotonin reuptake inhibitor (SSRI). Such agents have typically been administered orally. In particular, the method of the invention comprises introducing SSRI agents into the systemic circulation via intravaginal or rectal administration. The delivery methods in the present invention avoid the peaks in plasma concentration observed in oral delivery and result in consistent plasma levels of active agent that may be sustained over a long period of time.

Because SSRIs delivered according to the present invention pass through the mucosal wall of the vagina or rectum, the active agent directly enters the systemic circulation. These methods provide the ability to control the rate of delivery of the agent with immediate release or longer duration of action based on controlled release from the delivery vehicle. This invention, therefore, provides a useful and advantageous method of systemically delivering SSRIs, in particular fluoxetine.

The persent invention also provides methods of treating depression, migraine headaches, obesity chronic pain, psychoactive substance abuse disorders, pre-menstrual dysphoric disorders (PMDD) and obsessive compulsive disorders substantially free of adverse effects that would be associated with peaks in plasma concentration. The preferred methods of treatment comprise administering the agent to a female intravaginally. The intravaginal delivery of SSRIs provide advantages over conventional treatments with orally delivered active agent including all or some of the following: (1) a reduction of side effects due to decreased serum concentration and/or reduced first pass metabolism, (2) a lower effective circulating concentration (systemic load), (3) the ability to control the rate of delivery of the agent with immediate release or longer duration of action based on controlled release from the vehicle and (4) freedom from peaks in plasma concentration as generally observed in oral delivery.

The following terms and phrases as utilized in the instant specification and claims have the meanings given below. The term "fluoxetine" refers to fluoxetine base, optically resolved fluoxetine and related compounds (e.g., salts) thereof. Fluoxetine is a base capable of forming salts with organic and mineral acids to form, for example, fluoxetine hydrochloride, a preferred form.

The term "excipient" refers to a pharmaceutically acceptable diluent, adjuvant, carrier, or vehicle with which fluoxetine is administered. Such excipients can be sterile liquids, including those of petroleum, animal, vegetable or synthetic origin, such as peanut oil, soybean oil, mineral oil, sesame oil and the like. A particular example of an excipient having applications in the method of the subject invention comprises tin catalyzed silicone polymer. The term "biocompat-ible" refers to a material having the property of being biologically compatible by not producing a toxic, injurious, or immunological response in living tissue. The phrase "pharmaceutically acceptable" refers to molecular entities, excipients, and compositions that are physiologically tolerable and do not generally produce an allergic or similar untoward reaction, such as gastric upset, dizziness and the like, when administered to a human. Preferably, as used herein, the term "pharmaceutically acceptable" means substances approved for use in the body.

The phrase "therapeutically effective amount" as used herein, means that amount of an SSRI, in particular fluoxetine or a pharmaceutically acceptable salt thereof, which, alone or in combination with other drugs, provides a therapeutic benefit in the prevention, treatment, or management, of depression, anxiety, bulimia, obesity, obsessive compulsive syndrome migraine, pre-menstrual dysphoric disorder (PMDD) and other disorders affected by serotonin levels or one or more symptoms thereof. Different therapeutically effective amounts may be applicable for each disorder, as will be readily known by those of ordinary skill in the art.

As used herein, the phrase "controllably released" refers generally to the release of fluoxetine from a vaginal delivery device of the invention, e.g. a vaginal ring, wherein the SSRI agent is released to the body over an extended period of time, e.g. up to several weeks. Controlled release may be effected through art-recognized mechanisms, such as reservoir and matrix controlled release. In the former, the SSRI is contained with one or more excipients in a reservoir within the device having thereover a membrane that permits gradual passage of the SSRI therethrough over the desired period of time. In the matrix technique, the excipient and/or the biocompatible elastomer of the device retards the release of the SSRI agent, preferably fluoxetine, contained therein, thereby preventing immediate release of all of the full dosage to the vaginal mucosa. In a particular embodiment, the release of fluoxetine ranges from about 5 mg/day to about 80 mg/day for periods of ranging from a plurality of days up to several weeks. A particular example of an elastomer/excipient having controlled release applications herein comprises trifluoropropylmethyl/dimethyl siloxane elastomer, which is represented by the formula below

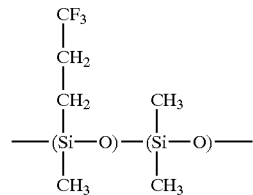

"Treating" as utilized herein covers treatment of an existing condition, inhibiting the progress or development of the condition, ameliorating the condition, and providing palliation of the condition. It is preferred that the agents of this invention are employed in the treatment of depression, anxiety, bulimia, obesity, obsessive compulsive syndrome, migraine, and pre-menstrual dysphoric disorder (PMDD).

When administered intravaginally or rectally, SSRIs can be formulated neat or using a variety of pharmaceutical carriers which are amenable for such administration including creams, gels, foams, tablets, suppositories and pessaries, containing a number of synthetic or natural materials including, but not limited to, silicones, polycarbophils, polyethylene glycols, and hydrogels. Such carriers may be nontherapeutic or therapeutic in and of themselves. Therapeutic carriers with beneficial medicinal properties can be used, for example, to control vaginal pH, treat or inhibit sexually transmitted diseases, or provide vaginal hydration.

Compositions for use in the methods of the invention include compositions wherein the active ingredient is contained in an effective amount to achieve its intended purpose. The compounds can be administered in any pharmaceutically acceptable amount, for example, in amounts ranging from 0.001 gram to about 1 gram per kilogram of body weight. Based on the information presented herein, the determination of effective amounts is well within the skill of the ordinary practitioner in the art. The compounds are generally used in pharmaceutical compositions containing the active ingredient with a suitable carrier or vehicle in the composition in an amount of about 0.1 to 99 wt %, preferably from about 4–60% by weight of a SSRI and from about 40–96% by weight of a suitable carrier. A preferred dosage for fluoxetine administered intravaginally in an extended release formulation of the invention is 90 mg administered 1 time per week. Using the methods and compositions disclosed herein, one of ordinary skill in the art can readily formulate dosage regimens to deliver the desired amount of agent over much longer or shorter periods of time.

Particular drug formulations of the present invention may be delivered via a vaginal delivery device designed to release therapeutic levels of the drug. Devices useful in the method of the invention are disclosed in U.S. Pat. No. 6,264,973, issued Jul. 24, 2001, intravaginal administration of an anesthetic agent, and pending U.S. patent application Ser. No. 09/531,851, filed Mar. 2, 2000, intravaginal administration of oxybutynin, the disclosure of which is incorporated herein by reference.

Figure 1B:
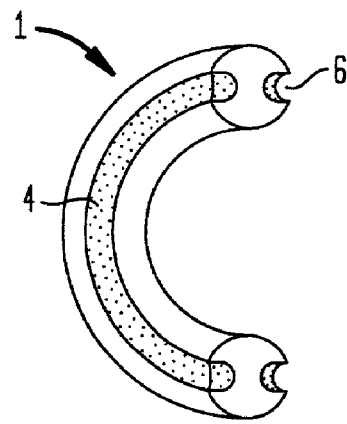
FIG. 1B is a schematic cross sectional and side view of a vaginal ring device.

FIGS. 1A and 1B illustrate one embodiment of the invention which comprises a vaginal ring device with one or more channels in its surface for receiving a drug formulation of the invention which can dispense therapeutic levels of drug to a female. FIG. 1A displays a top view of the vaginal ring device 1 with channel 4 in view, whereas FIG. 1B is a side view of the vaginal ring device 1 which displays channels 4 and channel 6. The ring device 1 can be comprised of a variety of materials, including but not limited to polytetrafluoroethylene, polydimethylsiloxane, trifluoropropylmethyl/dimethyl siloxane and various other silicone elastomers, or a mixture thereof. In the embodiment illustrated in FIGS. 1A and 1B, the width of the entire ring device 1 is typically 5.7 cm, and the cross-sectional diameter of the ring is typically 8 mm. The channels 4 and 6 can vary in depth and width depending on the drug formulation it will hold. Certain formulations, for instance, the composition described in Example 4 below are effectively delivered using this device.

Figure 2:
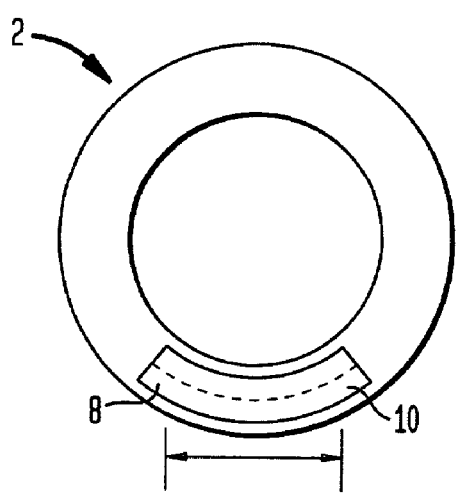
FIG. 2 is a schematic cross sectional view of a trifluoropropyl pocket ring.

FIG. 2 displays another vaginal delivery device comprising a trifluoropropylmethyl/dimethyl siloxane elastomeric ring having a pocket molded therein to receive a drug formulation of the invention. Therapeutic levels of drug are released over an extended period of time by diffusing through the elastomeric material of this ring at a controlled rate. FIG. 2 schematically shows a top view of the trifluoropropylmethyl pocket ring 2 with a slit 8 that creates an entrance to the pocket 10. The width of the entire ring 2 is typically 5.7 cm, and the cross-sectional diameter of the ring is typically 8.5 mm. This device has applications in mammalian females. Due to natural variation among mammalian females, the size and dimension of this ring 2 will vary, so that it is of sufficient size to be inserted into the vaginal canal of the female.

Figure 3A:
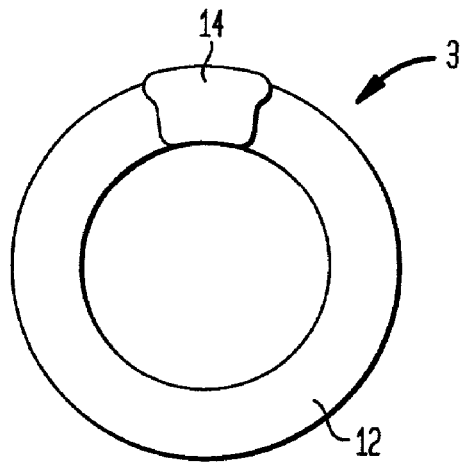
FIG. 3A is a schematic top view of a hollow toroid assembly.
Figure 3B:
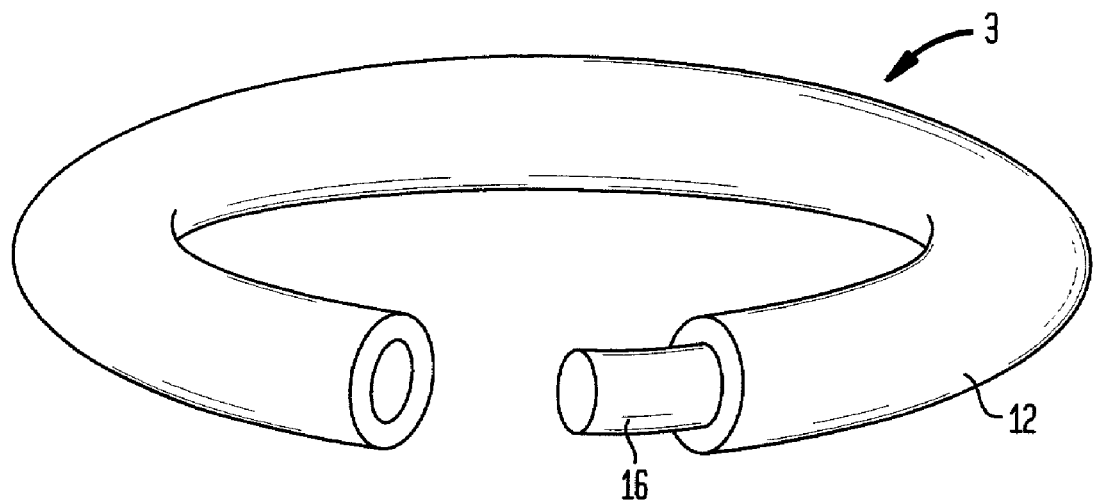
FIG. 3B is a schematic cross-section of a hollow toroid assembly.

FIGS. 3A and 3B display a vaginal ring comprising a hollow toroid assembly consisting of variable thickness polydimethylsiloxane tubing formed into a toroidal shape for use in higher dose delivery of an SSRI in accordance with the subject invention. The hollow toroid assembly 3 is a silicon tubing 12 that is connected with a solid piece of silicon 14. The cross-sectional diameter of the silicon tubing is typically 8.5 mm, and the width of the entire tubing when in the shape of a ring is typically 5.7 cm. As seen in FIG. 3B, the tubing 12 is filled with a drug composition 16, such as a fluoxetine composition, prior to the application of the solid piece of silicon 14 which holds the tubing 12 in the form of a ring. The polydimethylsiloxane elastomer in this ring does not retard the release of the drug to the same extent as the trifluoropropylmethyl/dimethyl siloxane elastomer of the device illustrated in FIG. 2.

Figure 4A:
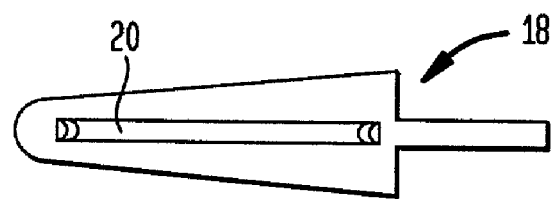
FIG. 4A is the schematic top view of an intravaginal insert used in a fluoxetine rabbit study.
Figure 4B:
FIG. 4B is the schematic side view of an intravaginal insert used in the fluoxetine rabbit study.
Figure 5:
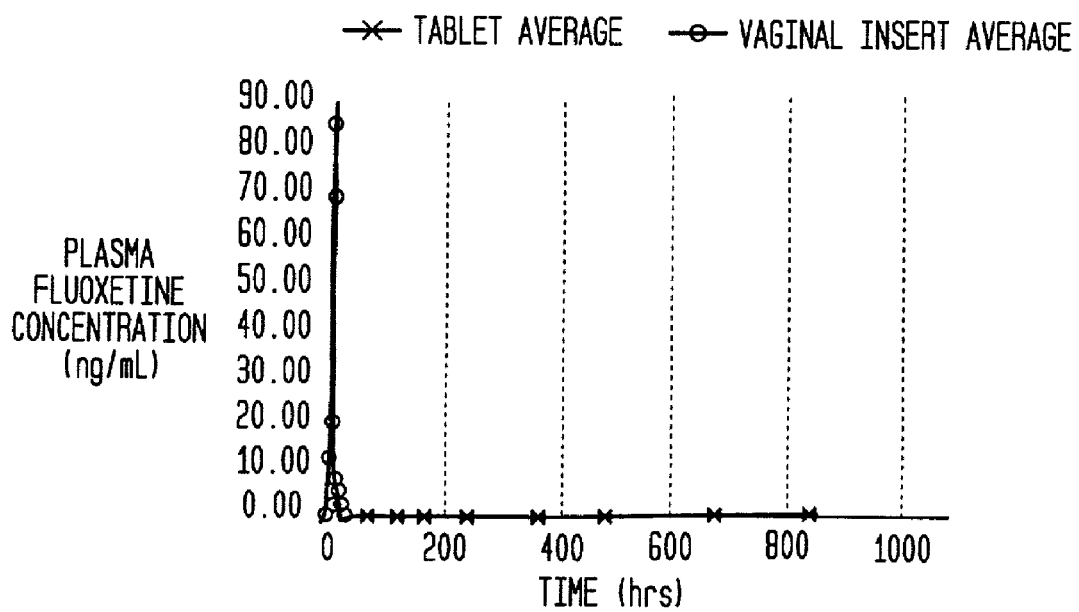
FIG. 5 is a graph comparing the average plasma levels of fluoxetine in rabbits via oral administration versus intravaginal administration over a thirty five-day period.
Figure 6:
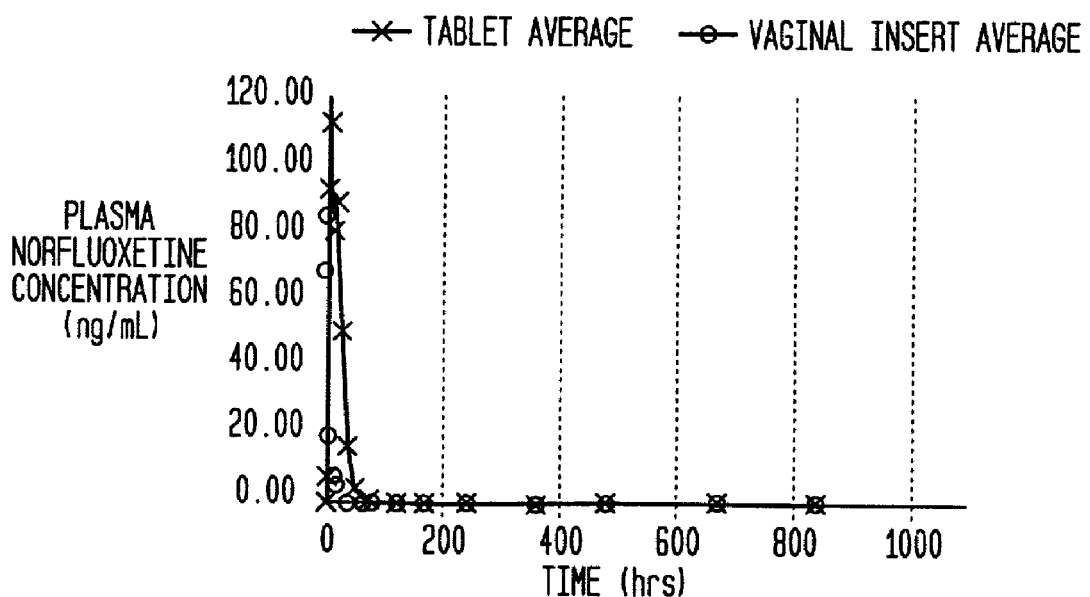
FIG. 6 is a graph comparing the average plasma levels of norfluoxetine in rabbits over a thirty five-day period following administration of fluoxetine orally versus intravaginally.
Figure 7:
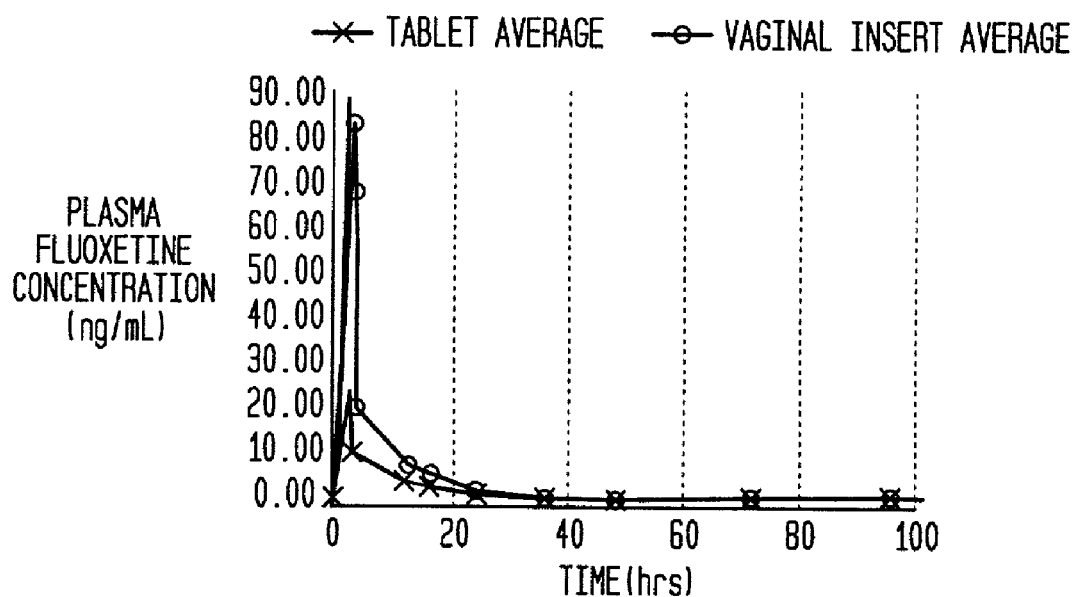
FIG. 7 is a graph comparing the average plasma levels of fluoxetine in rabbits via oral administration versus intravaginal administration of fluoxetine over a ten-day period.
Figure 8:
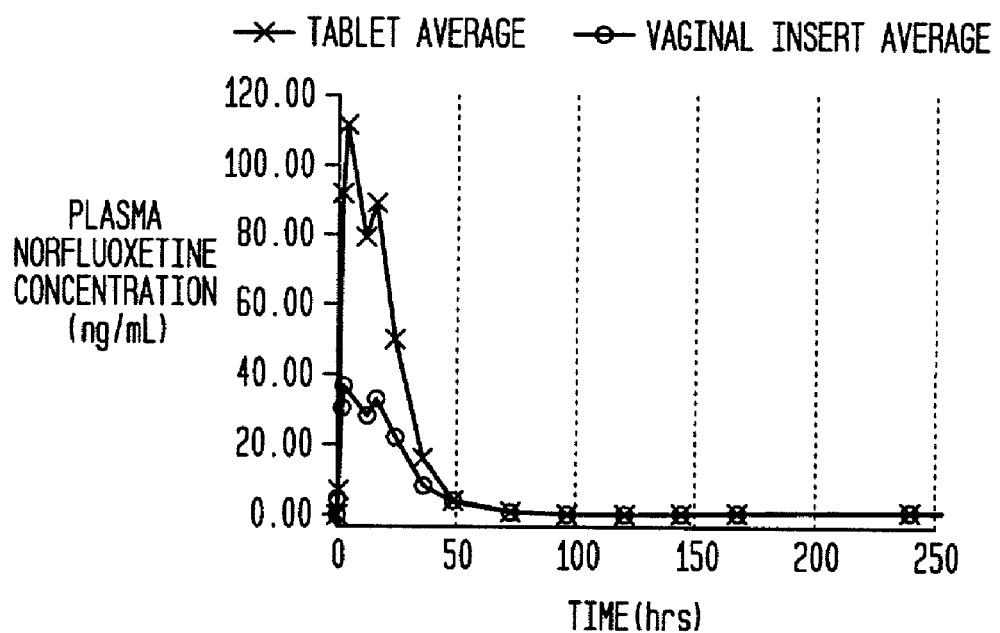
FIG. 8 is a graph comparing the average plasma levels of norfluoxetine in rabbits over a ten-day period following administration of fluoxetine orally versus intravaginally.

FIG. 4A is a top view of an intravaginal insert 18 especially for use in experimental animals. Channel 20 in the surface of the devices provides for a location for the placement of suitable drug formulations for intravaginal administration. FIG. 4B is the side view of the intravaginal insert 18 shown in FIG. 4.

The present invention may be better understood by reference to the following non-limiting Examples. The Examples are representative of intravaginal or rectal formulations and their preparation and are presented in order to more fully illustrate the preferred embodiments of the invention. They should in no way be construed as limiting the broad scope thereof.

EXAMPLE 1

Thermoplastic C-Flex Ring Made from Polyproplyene/Silicone/Mineral Oil/Styrene Ethylene Butadiene Styrene Copolymer Having a First Channel on the Upper Surface of the Ring, and a Second Channel on the Lower Surface of the Ring First and second channels Are drilled into the upper and lower surfaces, respectively, of a thermoplastic C-flex ring made from polyproplyene/silicone/mineral oil/styrene ethylene butadiene styrene copolymer and having a diameter of 5.7 cm and a cross-sectional width of 8 mm. Such a ring is schematically shown in FIGS. 1(A) and (B). The first and second channels have a width of 3 mm, and a depth of 3 mm. The first and second channels are filled with a pharmaceutical composition, such as the Gelucire fluoxetine paste composition described in Example 2. The release of fluoxetine from the ring is dependent on the pharmaceutical composition used to fill the channels.

EXAMPLE 2

Gelucire Fluoxetine Paste

A paste is prepared from 96% by weight Gelucire 44/14 (Gattefosse S. A., Saint-Priest Cedex, France) and 4% by weight Fluoxetine Hydrochloride. The Gelucire 44/14 is melted by heating to 80° C., add the Fluoxetine Hydrochloride and mix the composition for thirty minutes. The resulting paste is filled into the channels of the vaginal ring made in Example 1. The ring is then refrigerated to allow the composition to congeal.

EXAMPLE 3

Fluoxetine Silastic Ring Composition

A pharmaceutical composition is prepared from the following formulation:

| Ingredient | Amount |
| --- | --- |
| Fluoxetine HCl | 3.86 g (30%) |
| MED-6602 Silicone Base | 8.00 g (62.22%) |
| Tin Catalyst mixture | 1.00 g (7.78%) |

The MED-6602 silicone base and tin catalyst mixture are mixed for 16 seconds using a high-speed orbital mixer. The fluoxetine HCl is added in increments to the pre-mixed silicones, stirring the mix for 16 seconds between each addition. After all of the fluoxetine is incorporated, mixing is continued for 26 seconds in the orbital mixer until the mixture is smooth.

EXAMPLE 4

Preparation of a Trifluoropropylmethyl/Dimethyl Siloxane Elastomer Ring for Low Dose and/or Extended Release.

A total of 40 g part A and 40 g part B trifluoropropylmethyl/dimethyl siloxane elastomer formation (NuSil Technology, CF2-3521 grade) are weighed into a 100 g capacity Hauschild mixing cup and subsequently mixed for 10 seconds in a Hauschild Model 501 T speed mixer. A metal spatula is used to scrape down the sides of the mixing cup and further blend the two starting components. A final 14-second speed mixer cycle is utilized to ensure blend uniformity.

The trifluoropropylmethyl/dimethyl siloxane elastomer mixture is then compressed between the unheated platens of a Gluco injection molding machine for sixty seconds at 150° C. The mold is constructed such that a pocket and slit are molded into the ring. The compressed, filled mold assembly is then placed between the preheated platens of a model Carver press. A pressure of 5,000 psi is applied and the assembly is heated at 150° C. for 15 minutes to cure the elastomer. The cured ring is separated from the mold by hand.

For low dose and/or extended controlled release delivery, the appropriate dosage and appropriate ring pocket size are determined to receive a suitable fluoxetine composition, for example, the composition of Example 3. After the pockets of the ring are filled with the silastic-fluoxetine mixture of Example 3, the ring is allowed to cure for 48 hours.

EXAMPLE 5

Fluoxetine Silastic High Dose Transvaginal Ring

For high dose delivery, a hollow toroid ring comprising polydimethylsiloxane elastomer as shown in FIG. 3 of appropriate tubing thickness is filled with the silastic-fluoxetine mixture of Example 3. The filled ring is allowed to cure for 48 hours.

EXAMPLE 6

Fluoxetine Hydrogel

A hydrogel containing fluoxetine is prepared from the following composition:

| Ingredient | Amount per 100 g of Hydrogel |
| --- | --- |
| Water | 37.5 |
| Carbomer | 0.50 |
| Natrosol (HEC) | 2.50 |
| PEG-400 | 20.0 |
| Propylene Glycol | 20.0 |
| Ethanol | 12.5 |
| Fluoxetine | 5.0 |
| Preservative system | 2.00 |

The carbomer is dispersed in water with high agitation, and mixed for about 10–15 minutes until the carbomer swells and a homogeneous mixture forms, gradually heating the solution to 45° C. Concurrently, Natrosol is dispersed into the PEG-400 and Propylene Glycol, mixing for 15 minutes at 300–400 rpm, gradually bringing the temperature to 45° C. The carbomer and water mixture is added to the Natrosol mixture, mixing until homogeneous. The Fluoxetine and ethanol are mixed to form a solution which is then added to the hydrogel base mix. Finally, the preservative system comprising methylparaben, propylparaben, and benzyl alcohol is added to the mixture and mixing continued until the gel forms and room temperature (25–27° C.) is achieved.

EXAMPLE 7

| Foaming Gel | |
| --- | --- |
| Ingredient | Amount per 100 g |
| Water | 68.3 |
| Natrosol (HEC) | 0.20 |
| Fluoxetine | 10.0 |
| Acrylic co-polymer | 6.70 |
| Aminomethylpropanol | 0.60 |
| Cocotrimonium methosulfate | 2.00 |
| Ceteareth-25 | 0.20 |
| Preservative | 2.00 |
| Propellant | 10.0 |

The Natrosol is dissolved in water until the mixture appeared to be clear. The remaining ingredients are added in the following order: fluoxetine, acrylic co-polymer, aminomethylpropanol, cocotrimonium methosulfate, ceteareth-25 and preservative. The mixture is agitated until homogeneous, poured into appropriate containers and charged with propellant.

EXAMPLE 8

| Suppositories | |
| --- | --- |
| Ingredient | Amount per 100 g |
| Gelucire 44/14 | 82.0 |
| Modified Cornstarch | 3.00 |
| Fluoxetine | 10.0 |
| Brij 30 | 5.00 |

Melt the Gelucire to 80° C. Disperse the corn starch into the molten Gelucire and mix this for 10 minutes. Add the fluoxetine and disperse. Mix for 10 minutes. Add the Brij 30, and cool the mixture with constant stirring. Pour the fluoxetine mass into suppository molds at 50–55° C. and refrigerate until suppositories are formed.

EXAMPLE 9

Lotions and creams

| Ingredient | Amount per 100 g of Lotion |
| --- | --- |
| Deionized Water | q.s. to 100 |
| Modified starch | 1.75 |
| Fluoxetine | 10.0 |
| Dimethicone | 7.50 |
| Dimethicone copolyol | 2.50 |
| Brij 78 (steareth-20) | 1.00 |
| Cetearyl alcohol | 2.00 |
| Preservative system | 2.40 |
| Propylene glycol | 5.0 |
| Corn starch modified | 3.0 |
| Water | 20.0 |

First, prepare a starch slurry by dissolving the modified starch in 10 g of deionized water, stirring until a thick paste forms. Add the slurry to water at room temperature, and then heat the resulting mixture to 80° C. with constant stirring, using a Lightnin® mixer. While stirring, add the fluoxetine to the starch solution and disperse. Continue mixing for 20 minutes using 260–300 rpm shear. Mix dimethicone, dimethicone copolyol, Brij 78 and cetearyl alcohol together, and then add it to the starch mixture. Increase the temperature of the mixture to 85–90° C. After ten minutes, turn off the heat, allowing the mixture to cool down, and add the preservative system consisting of methylparaben, propylparaben and benzyl alcohol, at 70° C. Mix the propylene glycol with the corn starch modified, and then combine this mixture with the water. Allow the mix to cool down. Finally, at 60–65° C., add the glycol-corn starch-water mixture. Stir until a smooth lotion forms.

EXAMPLE 10

Long Acting Film Gels

| Ingredient | Amount per 100 g |
| --- | --- |
| Carageenan (Gelcarin) | 15.0 |
| Water | 75.0 |
| Fluoxetine | 10.0 |

Mix fluoxetine and water at high agitation over a steam bath until slightly homogeneous. Add the carageenan and disperse for 5–10 minutes. Mix for 20 minutes and then pour over a film table and form films to the desired thickness. Allow to dry.

EXAMPLE 11

Quick Dissolve Film

| Ingredient | Amount per 1 g of 2.5 cm$^2$ |
| --- | --- |
| HPMC K44 | 1.5 |
| Water | 10.0 |
| Mineral Oil | 10.0 |
| Water | 33.5 |
| Ethanol | 35.0 |
| Fluoxetine | 10.0 |

Heat ten percent of the water to 80° C. and disperse HPMC in the hot water. Once dispersed, immediately transfer the HPMC dispersion to the remaining cool water and mix for thirty minutes at room temperature. Concurrently mix the mineral oil and fluoxetine together, creating a thick slurry. Slowly add the ethanol to the mineral oil/fluoxetine slurry then add to the HPMC gel and disperse, stirring for thirty minutes. Form films to desired thickness and place in a 60° C. oven and allow to dry.

EXAMPLE 12

Vaginal Spray

| Ingredient | Amount per 100 g |
| --- | --- |
| Deionized Water | 76.1 |
| Polysorbate 80 | 0.40 |
| Fluoxetine | 10.0 |
| Ethanol | 10.0 |
| Preservative System | 2.50 |
| PG. and diazolidinyl urea | 1.0 |

Mix the deionized water, polysorbate 80 and the fluoxetine together, and heat the mixture to 80° C. with constant stirring until the fluoxetine fluoxetine is finely dispersed. Cool to 40° C. and then add the ethanol, preservative system consisting of methylparaben, propylparaben and benzyl alcohol, the PG and diazolidinyl urea simultaneously. Stir the mixture for an additional thirty minutes and then allow to cool to room temperature. Transfer to an appropriate spray or aerosol container.

EXAMPLE 13

Rabbit Study

A study was designed to compare the pharmacokinetic profiles of oral vs. intravaginal administration of fluoxetine in white albino female New Zealand rabbits. The study compared the blood levels of fluoxetine and/or its metabolites in the rabbits after either a single oral dose or a single intravaginal dose of fluoxetine hydrochloride. Both oral (tablet) and intravaginal (transvaginal insert) administration delivered the standard human daily dose of 20 mg fluoxetine hydrochloride to each rabbit. The oral route was used to compare the bioavailability of fluoxetine by the two routes of administration.

Based on previous rabbit studies (Byrd and Markham, 1994), repeated daily doses of fluoxetine of up to 7.5 mg/kg/day were fairly well tolerated and were associated with reductions in food consumption and body weight, but were not associated with mortality. The rabbits in this study weighed between 3.0–4.0 kg and received a single dose of fluoxetine, equivalent to approximately 5.0–6.7 mg/kg. It was expected that fluoxetine administered either orally or intravaginally within this dose range would be well-tolerated by the rabbits in the study.

Three rabbits received the fluoxetine tablets orally, while three rabbits received fluoxetine inserts intravaginally. The fluoxetine tablets were administered orally using an animal pilling device. The fluoxetine inserts were administered by insertion into the vaginas of the rabbits. The inserts remained in place for 2–4 hours, after which they were removed. Removal was accomplished by using an appropriate instrument to grasp the extension on the back of the insert. If an insert was expelled from an animal before removal, it was noted but not replaced. Both tablets and intravaginal inserts were administered once on Day 0.

The animals were observed twice daily for mortality and general condition. Animals in poor health were identified and further monitored. In addition, observations were made for any signs of toxic or pharmacologic effects (e.g., abnormalities in general, appearance, activity, behavior, respiration, etc.). No mortality occurred during the length of the study. One animal from each treatment group (oral vs. intravaginal) was observed to have decreased food consumption. Mean body weights and body weight gains for both treatments were similar throughout the study. Based on the results of the study, no differences in clinical observations or body weights were noted between the compared administration methods.

Blood samples were obtained for the determination of plasma concentrations of fluoxetine. Starting on Day 0, blood samples were obtained for toxicokinetic determinations from all animals pretest and at 1, 3, 8, 12, 16, 24, 36, 48, 72, 96, 120, 144, 168, 240, 360, 480, 672 and 840 hours post-dose. Pre-dose samples were collected one week prior to dosing. Approximately 1.5 mL of whole blood was obtained from the medial auricular artery of the unanesthetized rabbits, unfasted, and were preserved using ethylenediamine tetraacetic acid (EDTA). The samples were stored appropriately at −70° C. or lower until plasma analysis could be performed.

The EDTA preserved rabbit plasma samples were analyzed for fluoxetine and norfluoxetine using a solid phase extraction (SPE) technique. The equipment used are seen in Table 1 below. The standards used were fluoxetine and norfluoxetine at concentrations between 1.00–75.00 ng/mL. A 0.5 mL aliquot from each sample and standard were spiked using an internal standard desipramine-d3 free base (100 μg/mL solution) in methanol. The internal standard spiking solution was diluted with methanol so that the final concentration of desipramine-d3 was equivalent to 20 ng/mL.

Samples were evaluated using a solid phase extraction technique using conditioned SPE cartridges, then analyzed via HPLC and mass spectroscopy. The parameters used are seen in Tables 2 and 3 below. Peak area from LC/MS/MS chromatograms were converted to ng/mL by interpolations employing constants generated by 1/x weighted linear regressions performed on the peak area ratio and calibration standard concentration data.

Plasma levels were obtained for fluoxetine and its metabolite, norfluoxetine. Analysis of the data showed that mean fluoxetine plasma levels were higher in rabbits who received fluoxetine intravaginally compared to the rabbits who received fluoxetine orally. Fluoxetine levels in both groups were almost undetectable after 72 hours. Analysis of the mean plasma levels for the fluoxetine metabolite showed the converse, however. Metabolite levels were observed to be much lower with intravaginal delivery compared to oral delivery. Mean norfluoxetine levels were present throughout most of the study in the oral group. Norfluoxetine levels began tapering off in the intravaginal group after about 10 days. Results of the analysis for both fluoxetine and norfluoxetine can be seen in the figures below.

Figure 9:
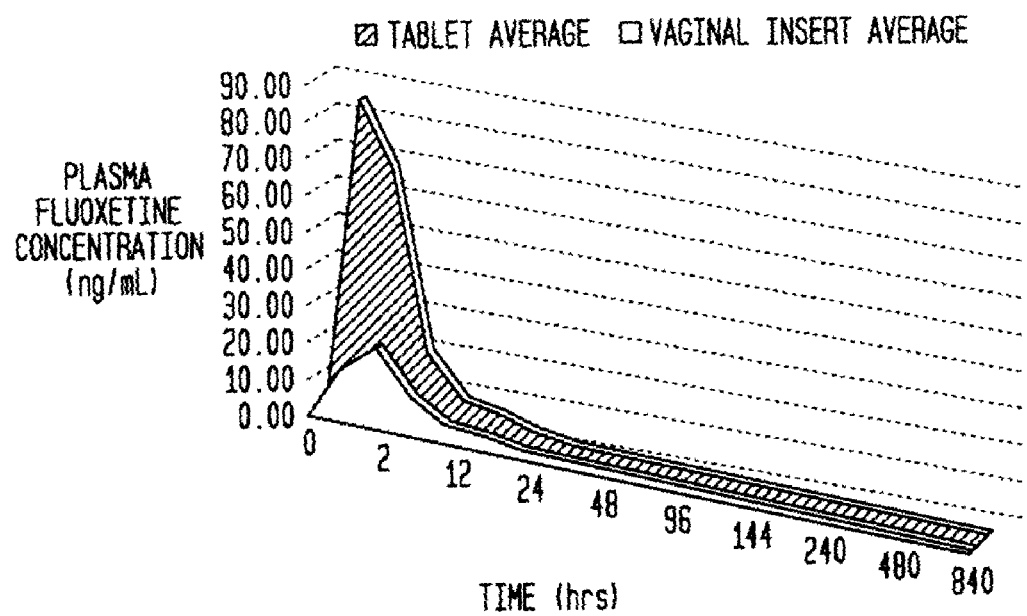
FIG. 9 is a graph comparing the average plasma levels of fluoxetine in rabbits via oral distribution versus intravaginal distribution over the period of 840 hours.
Figure 10:
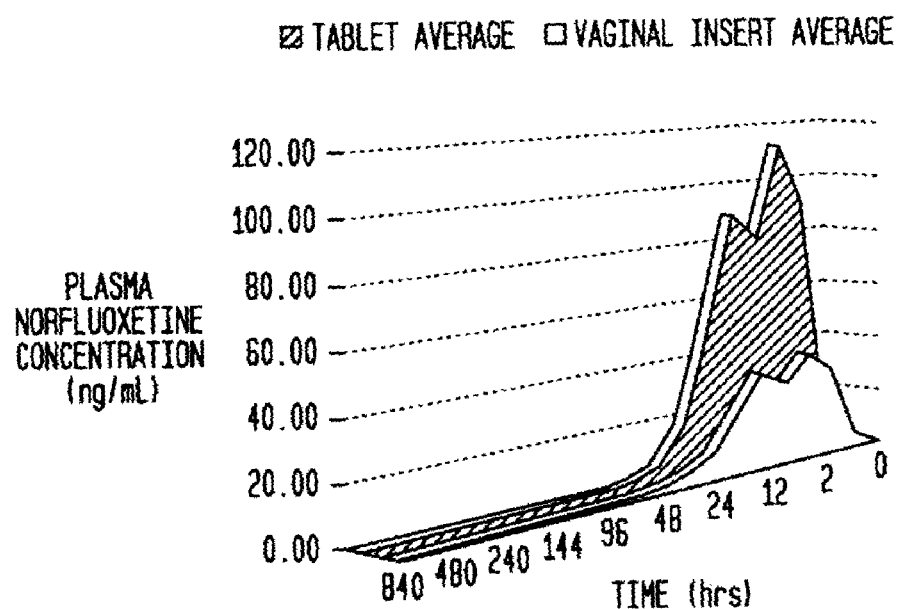
FIG. 10 is a graph comparing the average plasma levels of norfluoxetine in rabbits over a period of 840 hours following administration of fluoxetine orally versus intravaginally.

FIGS. 5–10 provide graphic results for the rabbit study. Based on the results of the study, it can be seen that fluoxetine can be effectively delivered vaginally. The results in FIG. 9 show that the average plasma level of fluoxetine in the rabbit via intravaginal administration is over 80 ng/ml after 1 hour as opposed to only about 10 ng/ml after 1 hour via tablet administration.

EXAMPLE 14

Standard Drug Release Profile (DRP) studies were conducted for the experimental fluoxetine composition used in the experiment outlined above with the following results:

| Time | % Release |
| --- | --- |
| DRP Results for Experimental Fluoxetine Composition | |
| 30 min. | 88 |
| 60 min. | 92 |
| 180 min. | 98 |
| DRP Results for Sarafem ® Tablets | |
| 30 min. | 93 |

Figure 11A:
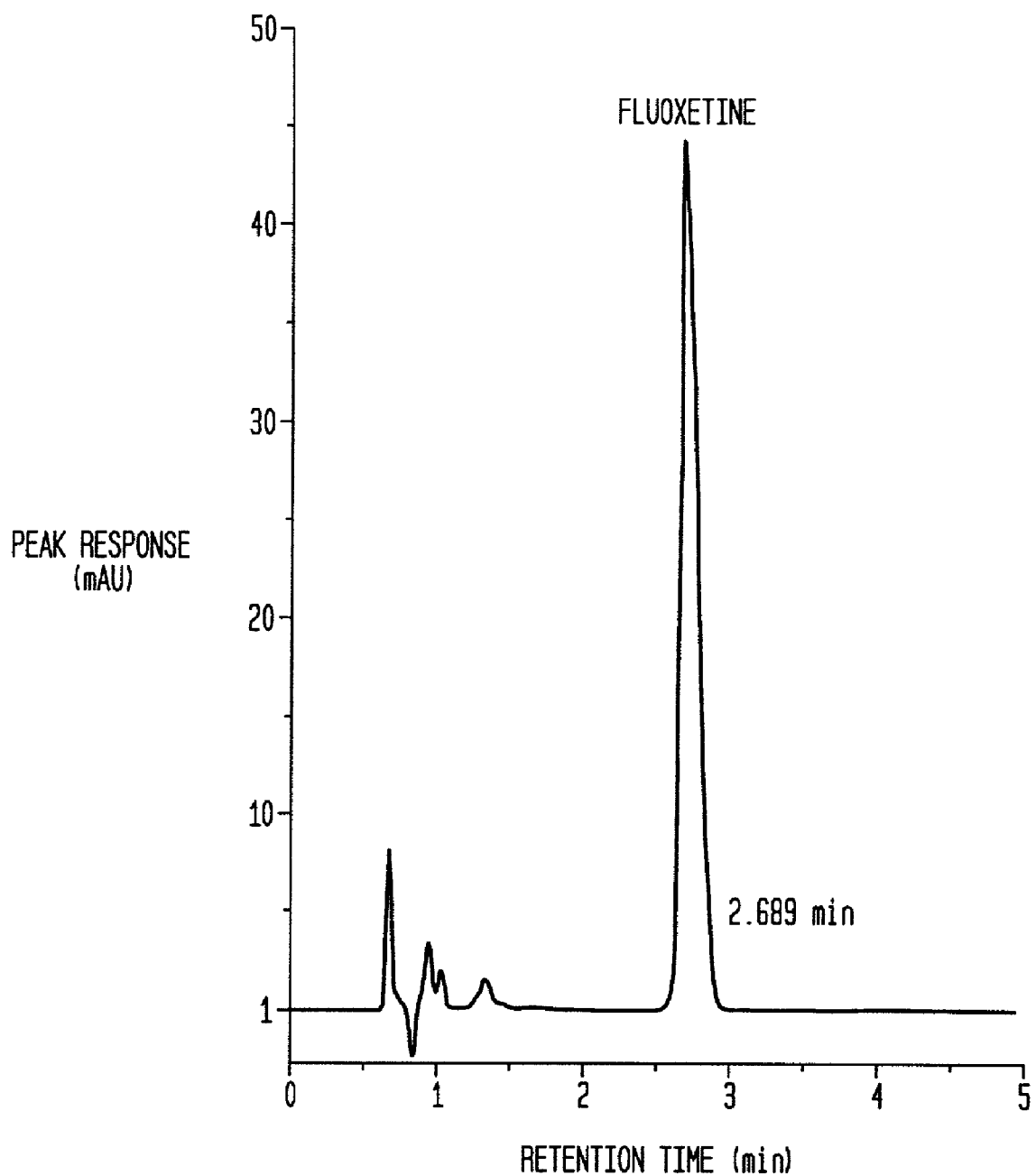
FIG. 11A is a HPLC chromatogram for a reference standard solution of fluoxetine in a Drug Release Profile study.
Figure 11B:
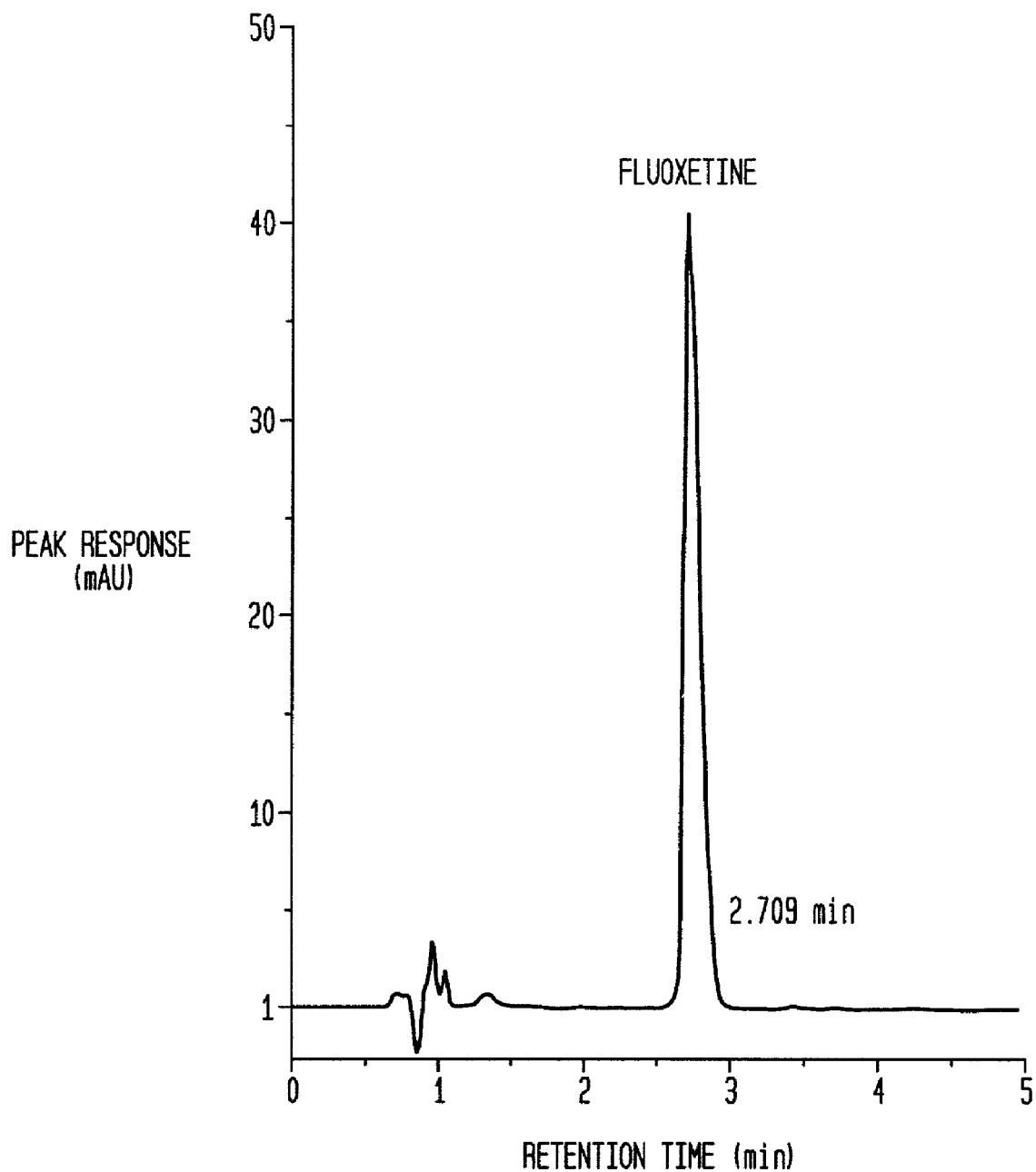
FIG. 11B is a comparative HPLC chromatogram for a fluoxetine formulation of the present invention in the Drug Release Profile study.
Figure 11C:
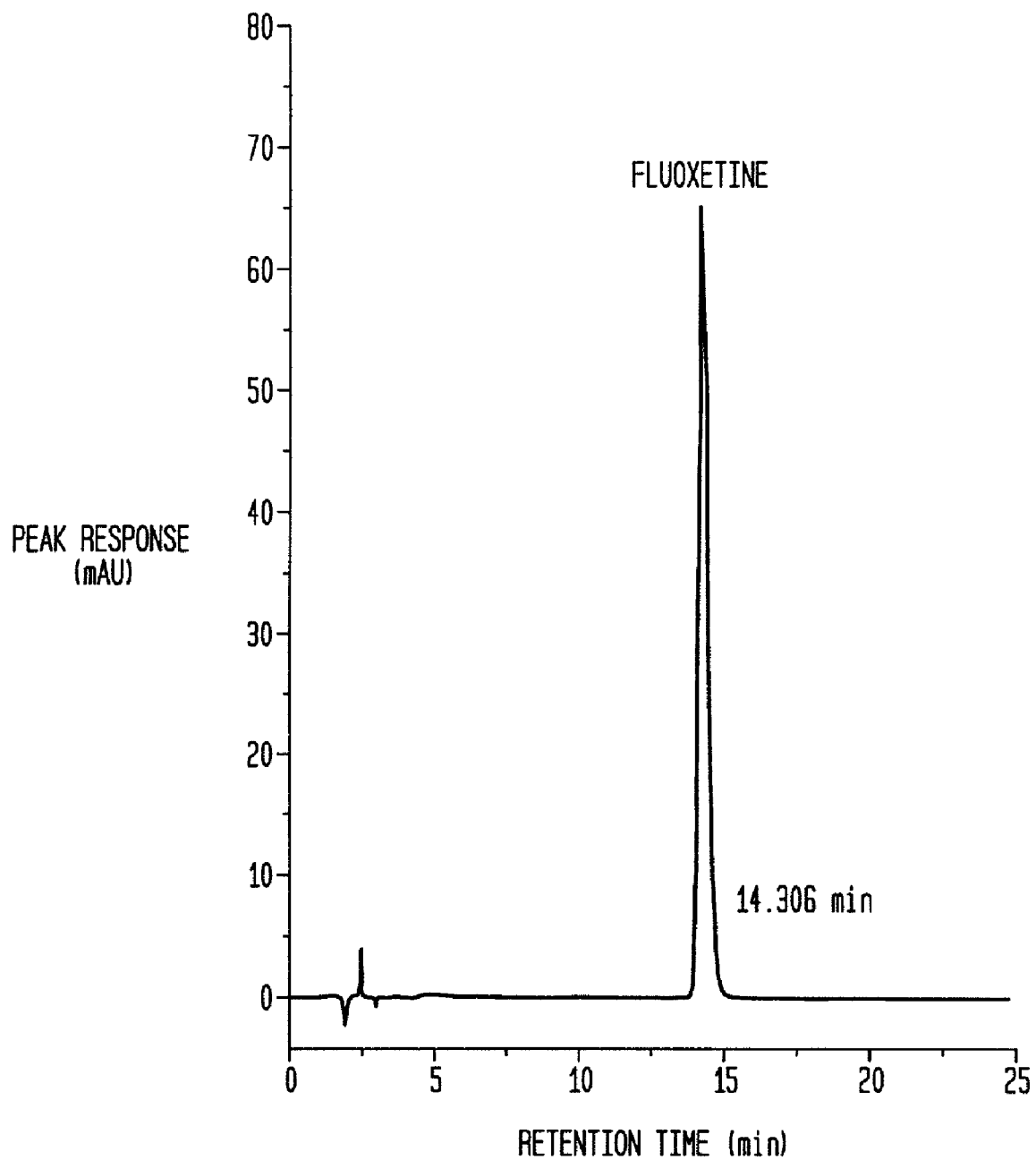
FIG. 11C is a typical chromatogram of reference standard solution for assay of fluoxetine.
Figure 11D:
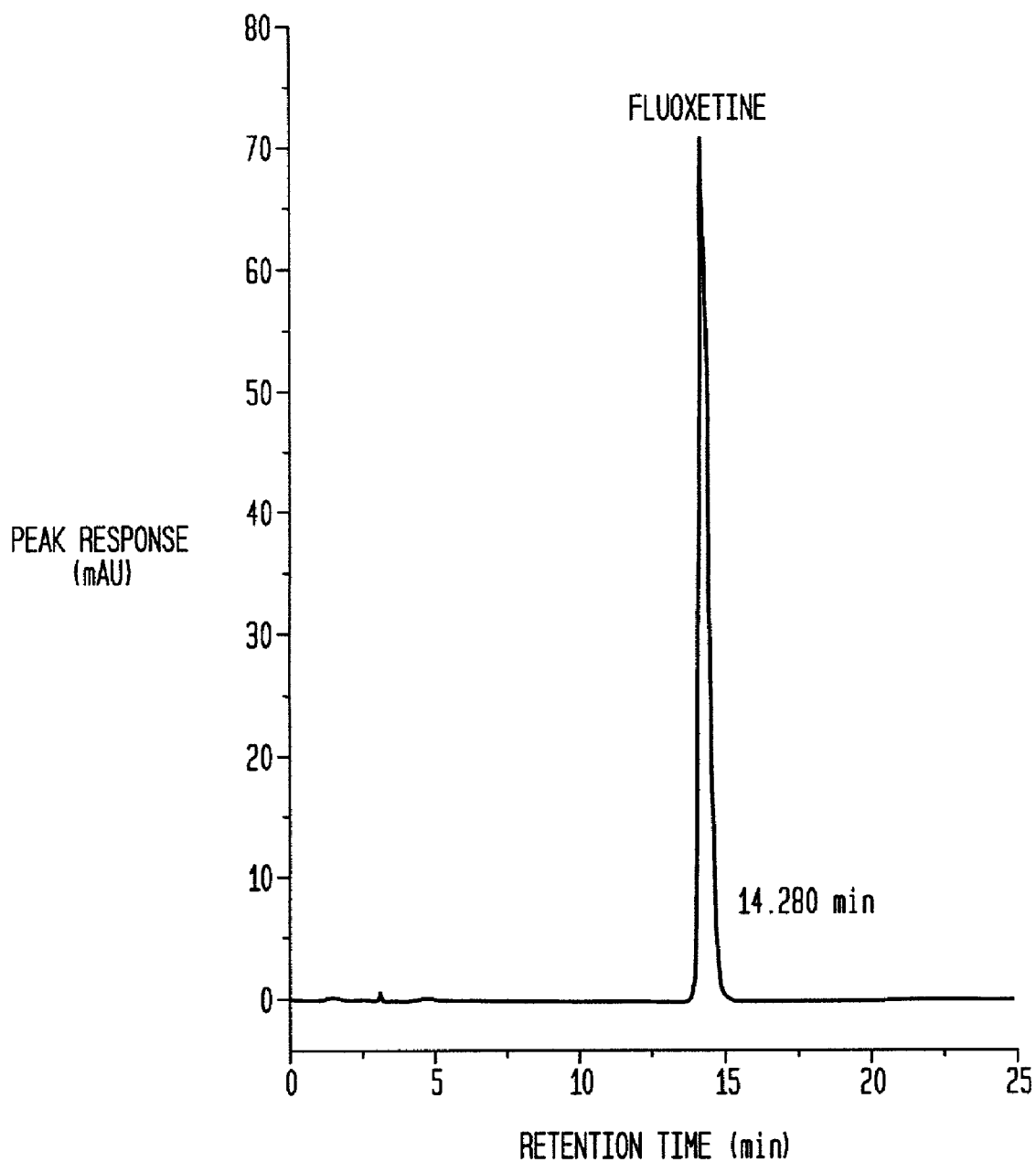
FIG. 11D is a typical chromatogram of a test sample solution for fluoxetine according to a formulation of the present invention.

Exemplary HPLC graphic results of Drug Release Profile Studies for the experimental test sample compared to standard are shown in FIGS. 11A–B. Fluoxetine in the experimental fluoxetine composition was assayed via HPLC. Exemplary HPLC graphic results for the experimental test sample compared to standard are show in FIGS. 11C–D. These results illustrate that fluoxetine is released from the subject compositions in a manner comparable to that of oral tablets.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A device, suitable for insertion into the vaginal canal of a female, for delivering and controllably releasing a selective serotonin reuptake inhibitor (SSRI) intravaginally over an extended period of time in a single application, to treat a disorder selected from the group consisting of depression, eating disorders, migraine headaches, pain, psychoactive substance use disorders, pre-menstrual dysphoric disorders (PMDD) and obsessive compulsive disorders, said device adapted to receive a pharmaceutical composition consisting of said SSRI as the sole active ingredient and suitable excipients, such that upon insertion of said device into the vaginal canal, a therapeutically effective amount of said SSRI is controllably released from said device over an extended period of time to treat said disorder.

2. A device in accordance with claim 1, wherein said SSRI is selected from the group consisting of fluoxetine, sertraline, paroxeline, fluvoxamine, citalopram and pharmaceutically acceptable salts thereof.

3. A device in accordance with claim 2, wherein said SSRI is fluoxetine or a pharmaceutically acceptable salt thereof and said composition consists of from about 4–60% by weight fluoxetine and from about 40–96% by weight of said suitable excipients.

4. A device, suitable for insertion into the vaginal canal of a female, for immediate delivery of a selective serotonin reuptake inhibitor (SSRI) intravaginally to treat a disorder selected from the group consisting of depression, eating disorders, migraine headaches, pain, psychoactive substance use disorders, pre-menstrual dysphoric disorders (PMDD) and obsessive compulsive disorders, said device adapted to receive a pharmaceutical composition consisting of said SSRI as the sole active ingredient and suitable excipients, such that upon insertion of said device into the vaginal canal, a therapeutically effective amount of said SSRI is immediately released from said device.

5. A device in accordance with claim 4, wherein said SSRI is selected from the group consisting of fluoxetine, sertraline, paroxetine, fluvoxamine, citalopram and pharmaceutically acceptable salts thereof.

6. A device in accordance with claim 5, wherein said SSRI is fluoxetine or a pharmaceutically acceptable salt thereof and said composition consists of from about 4–60% by weight fluoxetine and from about 40–96% by weight of said suitable excipients.

7. A device in accordance with claim 1, wherein said device is a vaginal ring.

8. A vaginal ring in accordance with claim 7, wherein said SSRI is selected from the group consisting of fluoxetine, sertraline, paroxetine, fluvoxamine, citalopram and pharmaceutically acceptable salts thereof.

9. A vaginal ring in accordance with claim 8, wherein said SSRI is fluoxetine or a pharmaceutically acceptable salt thereof said composition consists of from about 4–60% by weight fluoxetine and from about 40–96% by weight of said suitable excipients.

10. A device in accordance with claim 4, wherein said device is a vaginal ring.

11. A vaginal ring in accordance with claim 10, wherein said SSRI is selected from the group consisting of fluoxetine, sertraline, paroxetine, fluvoxamine, citalopram and pharmaceutically acceptable salts thereof.

12. A vaginal ring in accordance with claim 11, wherein said SSRI is fluoxetine or a pharmaceutically acceptable salt thereof and said composition consists of from about 4–60% by weight fluoxetine and from about 40–96% by weight of said suitable excipients.

* * * * *